United States Patent
Iuliano et al.

(10) Patent No.: US 9,717,457 B2
(45) Date of Patent: Aug. 1, 2017

(54) SENSOR, SYSTEM AND METHOD FOR MEASURING AND TRACKING IMPACTS SUSTAINED BY WEARER

(71) Applicants: Gerardo Iuliano, Vaughan (CA); Paul Norman Walker, Markham (CA)

(72) Inventors: Gerardo Iuliano, Vaughan (CA); Paul Norman Walker, Markham (CA)

( * ) Notice: Subject to any disclaimer, the term of this patent is extended or adjusted under 35 U.S.C. 154(b) by 0 days.

(21) Appl. No.: 14/594,167

(22) Filed: Jan. 11, 2015

(65) Prior Publication Data
US 2015/0196252 A1    Jul. 16, 2015

Related U.S. Application Data

(63) Continuation-in-part of application No. 13/685,868, filed on Nov. 27, 2012, now Pat. No. 9,247,780.

(51) Int. Cl.
| | |
|---|---|
| *G08B 21/00* | (2006.01) |
| *A61B 5/00* | (2006.01) |
| *A61B 5/11* | (2006.01) |
| *A61B 5/01* | (2006.01) |
| *A42B 3/04* | (2006.01) |

(52) U.S. Cl.
CPC .......... *A61B 5/6803* (2013.01); *A61B 5/0002* (2013.01); *A61B 5/11* (2013.01); *A61B 5/746* (2013.01); *A42B 3/046* (2013.01); *A61B 5/01* (2013.01); *A61B 2503/10* (2013.01); *A61B 2562/0219* (2013.01); *A61B 2562/06* (2013.01)

(58) Field of Classification Search
CPC .................................................... A61B 5/0002
USPC .................................. 340/684, 573.1, 686.1
See application file for complete search history.

(56) References Cited

U.S. PATENT DOCUMENTS

| | | | |
|---|---|---|---|
| 5,539,935 | A | 7/1996 | Rush, III |
| 5,978,972 | A | 11/1999 | Stewart et al. |
| 2006/0038694 | A1 | 2/2006 | Naunheim et al. |
| 2006/0189852 | A1* | 8/2006 | Greenwald .......... A61B 5/0002 600/300 |

(Continued)

FOREIGN PATENT DOCUMENTS

| | | |
|---|---|---|
| WO | 2007/062518 A1 | 6/2007 |
| WO | 2007/062519 A1 | 6/2007 |
| WO | 2012/100053 A1 | 7/2012 |

OTHER PUBLICATIONS

Rowson et al., "Brain Injury Prediction: Assessing the Combined Probability of Concussion Using Linear and Rotational Head Acceleration", Annals of Biomedical Engineering, Jan. 9, 2013.

(Continued)

*Primary Examiner* — Jeffery Hofsass
(74) *Attorney, Agent, or Firm* — Millman IP Inc.

(57) ABSTRACT

In an aspect, an accessory for an activity is provided, and includes an accessory housing, an impact detection device and a secondary module. The impact detection device includes at least one impact sensor selected from the group of sensors comprising an accelerometer and a gyroscope. The secondary module includes at least a battery configured for powering both the impact detection device and the secondary module. The impact detection device and secondary module together further include a microcontroller and a memory. The impact detection device is removably connectable to the secondary module and is connectable to another secondary module in another protective accessory.

6 Claims, 17 Drawing Sheets

(56) References Cited

U.S. PATENT DOCUMENTS

| | | |
|---|---|---|
| 2007/0056081 A1 | 3/2007 | Aspray |
| 2011/0218455 A1* | 9/2011 | Hennig ................ A63B 71/085 600/553 |
| 2012/0077440 A1 | 3/2012 | Howard et al. |
| 2012/0124720 A1 | 5/2012 | Evans et al. |
| 2012/0210498 A1 | 8/2012 | Mack |
| 2012/0306641 A1* | 12/2012 | Howard ................ A42B 3/046 340/539.11 |
| 2015/0000370 A1 | 1/2015 | Crossman et al. |

OTHER PUBLICATIONS

PCT/CA2013/000981, International Search Report, Feb. 27, 2014.

\* cited by examiner

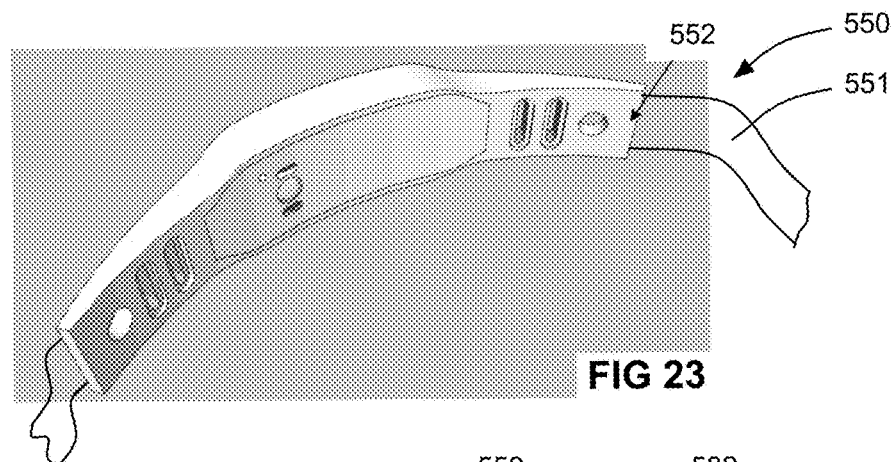
FIG 23
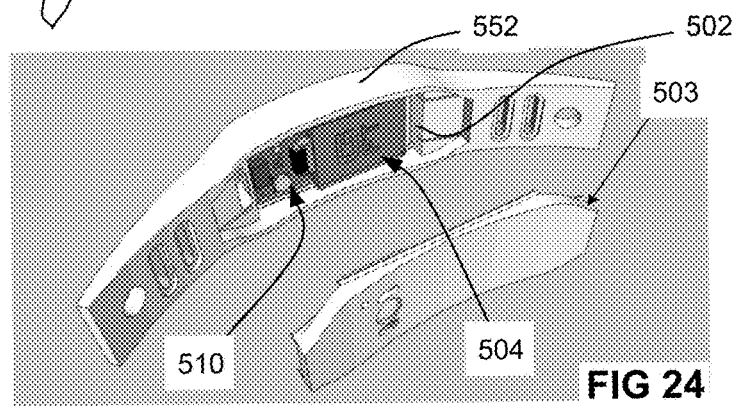
FIG 24
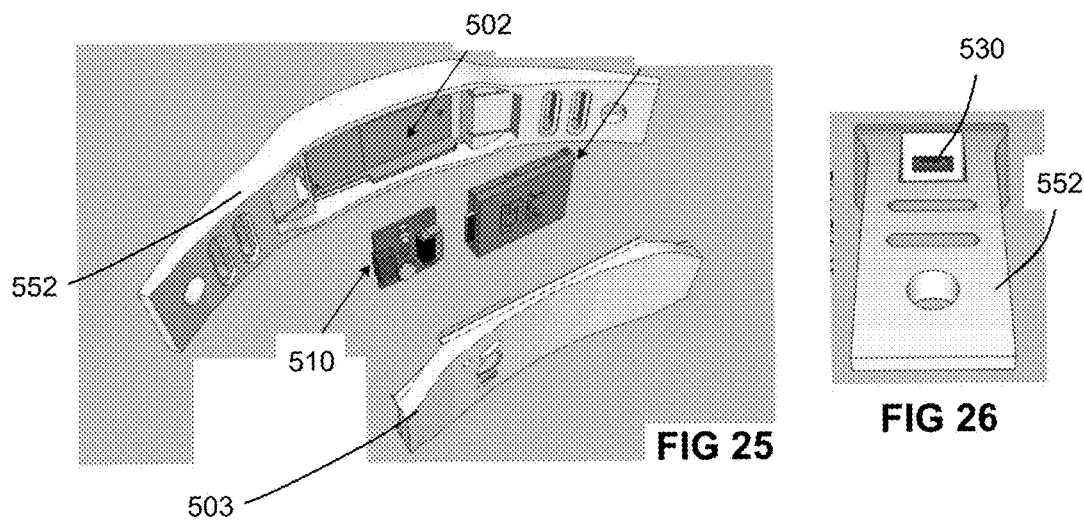
FIG 25
FIG 26

SENSOR, SYSTEM AND METHOD FOR MEASURING AND TRACKING IMPACTS SUSTAINED BY WEARER

CROSS-REFERENCE TO RELATED APPLICATIONS

This application is a continuation-in-part of, and claims the benefit of, U.S. patent application Ser. No. 13/685,868, filed Nov. 27, 2012, the contents of which are incorporated herein by reference in their entirety.

FIELD

The present invention relates to the activity accessories and impact detection equipment.

BACKGROUND OF DISCLOSURE

Sports-related concussions have skyrocketed in the U.S. with over 3.8 million reported each year. The timely detection of a concussion is vital because athletes who return to action too soon are vulnerable to repeat injuries. The damage can lurk inside, later surfacing as memory loss, a change in personality, depression and the early onset of dementia. Even in the absence of a concussion, multiple impacts might alert a coach to focus on a specific athlete's technique. Further, federal Centers for Disease Control and Prevention estimate that nearly a quarter-million youths 19 and under visited the emergency room for sports and recreation-related concussions in 2009. Medical experts suspect a far greater number did not seek medical attention or did not receive a diagnosis. It is recognized that early detection of concussions could drastically reduce injuries, according to the American Association of Neurological Surgeons, since most injuries occur because treatment is delayed. Further, more than 75 percent of concussions go undiagnosed, eventually contributing to over 30 percent of head trauma deaths in the U.S., according to the Centers for Disease Control and Prevention. Early detection also could cut medical bills and lost productivity.

Contact sports such as football, lacrosse and hockey present significant risks. Although helmets and other protective equipment (e.g. facial protection by visors, cages and/or goggles) used in these sports are protective, players can and do still suffer injuries such as a concussion. Even in the absence of a concussion, multiple impacts might alert a coach to focus on a specific athlete's technique. Current concussive science is of the understanding that even minor head trauma, if undetected, can lead to long-term damage. For example, Chronic Traumatic Encephalopathy (CTE) is a progressive degenerative disease, diagnosed post-mortem in individuals with a history of multiple concussions and other forms of head injury. CTE has been most commonly found in professional athletes participating in American football, ice hockey, professional wrestling and other contact sports who have experienced head trauma, and also in military service personnel exposed to a blast and/or a concussive injury. It is recognized that repeated concussions and injuries less serious than concussions ("sub-concussions") incurred during the play of contact sports over a long period can result in CTE. Another effect under current research is Second-Impact Syndrome (SIS), which is a condition in which the brain swells rapidly and catastrophically after a person suffers a second concussion before symptoms from an earlier one have subsided. This deadly second blow may occur days, weeks or even minutes after an initial concussion, and even the mildest grade of concussion can lead to SIS. Accordingly, researchers had developed an array of new technology, sensors that fit into helmets, some equipped to transmit impact data to the side-line, in order to help address early detection needed for potential CTE and SIS conditions.

However, although these new devices might suit college and professional teams, the new devices can be too expensive for youth sports and other broader based applications. Accordingly, more important that ever is the need for a widely adopted force detection device that is easily customizable and implementable in a variety of sports and other activities requiring helmet usage and other protective elements, while at the same time providing for one or more advantages such as reusability, easily identifiable once installed, and providing visual and/or audible indication of force impact events after they occur.

SUMMARY

It is an object of the present invention to provide an integrated protective assembly to obviate or mitigate at least one of the above-presented disadvantages.

Current impact detection equipment might suit college and professional teams, however this equipment can be too expensive for youth sports and other broader based applications. Accordingly, more important than ever is the need for a widely adopted force detection device that is easily customizable and implementable in a variety of sports and other activities requiring helmet usage and other protective elements, while at the same time providing for one or more advantages such as reusability, easily identifiable once installed, and providing visual and/or audible indication of force impact events after they occur. An additional need is the ability to detect and account for both linear acceleration and rotational acceleration effects occurring during an impact, as rotational acceleration can result in greater concussive effects over purely linear acceleration. Contrary to current protective equipment, there is provided an integrated protective accessory for a helmet comprising: a protective element for rigidly attaching to an external shell of the helmet via one or more fasteners; The protective element includes an impact detection device integrated with the protective element via one or more device fasteners such that a portion of the protective element has a compatible fastening element to that of the one or more device fasteners so that the impact detection device is rigidly attached to the protective element, the impact detection device having: a housing; one or more sensors within the housing for sensing an impact event of a wearer when wearing the helmet and for producing sensor data; an alarm element coupled to the housing such that an alarm condition produced by the alarm element is detectable by one or more persons near the wearer; and a processor within the housing for processing the sensor data against an impact threshold and for producing an alarm condition signal for expression by the alarm element as the alarm condition.

A first aspect provided is an integrated protective accessory for a helmet comprising: a protective element for rigidly attaching to an external shell of the helmet via one or more fasteners; an impact detection device integrated with the protective element via one or more device fasteners such that a portion of the protective element has a compatible fastening element to that of the one or more device fasteners so that the impact detection device is rigidly attached to the protective element, the impact detection device having: a housing; one or more sensors within the housing for sensing an impact event of a wearer when wearing the helmet and for producing sensor data; an alarm element coupled to the housing such that an alarm condition produced by the alarm element is detectable by one or more persons near the wearer; and a processor within the housing for processing the sensor data against an impact threshold and for producing an alarm condition signal for expression by the alarm element as the alarm condition.

A further aspect provided is an integrated protective accessory for a helmet comprising: a protective element for rigidly attaching to an external shell of the helmet including a pocket configured for receiving an impact detection device and a window positioned between the pocket and an external environment of the helmet; the impact detection device integrated with the protective element via one or more device fasteners such that a portion of the protective element has a compatible fastening element to that of the one or more device fasteners so that the impact detection device is rigidly attached to the protective element, the impact detection device having: a housing; one or more sensors within the housing for sensing an impact event of a wearer when wearing the helmet and for producing sensor data; an alarm element coupled to the housing such that an alarm condition produced by the alarm element is detectable by one or more persons near the wearer through the window; and a processor within the housing for processing the sensor data against an impact threshold and for producing an alarm condition signal for expression by the alarm element as the alarm condition.

A third aspect provided is an integrated protective sports accessory comprising: a protective eyewear element including a frame having a pair of lenses for protecting an area surrounding the eyes of a wearer and a strap for affixing the protective eyewear element to the head of the wearer; an impact detection device integrated with the protective eyewear element via one or more device fasteners such that a portion of the protective eyewear element has a compatible fastening element to that of the one or more device fasteners so that the impact detection device is rigidly attached to the protective eyewear element, the impact detection device having: a housing; one or more sensors within the housing for sensing an impact event of a wearer when wearing the protective eyewear element and for producing sensor data; an alarm element coupled to the housing such that an alarm condition produced by the alarm element is detectable by one or more persons near the wearer; and a processor within the housing for processing the sensor data against an impact threshold and for producing an alarm condition signal for expression by the alarm element as the alarm condition.

A further aspect provide is an integrated protective sports accessory comprising: a protective headwear element including a band for affixing the protective headwear element to the head of the wearer and a pocket attached to the band, the pocket configured for receiving an impact detection device and having a window positioned on the pocket suitable for exposing an impact detection device to an external environment of the protective headwear element; the impact detection device integrated with the protective headwear element as positioned in the pocket and retained therein via a pocket closure mechanism such that the impact detection device is rigidly coupled to the band, the impact detection device having: a housing; one or more sensors within the housing for sensing an impact event of a wearer when wearing the protective headwear element and for producing sensor data; an alarm element coupled to the housing such that an alarm condition produced by the alarm element is detectable by one or more persons near the wearer through the window; and a processor within the housing for processing the sensor data against an impact threshold and for producing an alarm condition signal for expression by the alarm element as the alarm condition.

The impact detection device can have one or more sensors including both an accelerometer and a gyroscope.

In another aspect, an accessory for an activity is provided, and includes an accessory housing, an impact detection device and a secondary module. The impact detection device includes at least one impact sensor selected from the group of sensors comprising an accelerometer and a gyroscope. The secondary module includes at least a battery configured for powering both the impact detection device and the secondary module. The impact detection device and secondary module together further include a microcontroller and a memory. The impact detection device is removably connectable to the secondary module and is connectable to another secondary module in another protective accessory.

BRIEF DESCRIPTION OF THE DRAWINGS

Exemplary embodiments will now be described in conjunction with the following drawings, by way of example only, in which:

FIG. 23 is a perspective view of a headband that holds the secondary module and the impact detection device;

FIG. 24 is a perspective view of the headband shown in FIG. 23 with a cover removed;

FIG. 25 is a perspective view of the headband shown in FIG. 23 with the cover, the secondary module and the impact detection device removed;

FIG. 26 is a side elevation view of the headband shown in FIG. 23 showing a micro-USB port thereon.

DETAILED DESCRIPTION OF EMBODIMENTS

Figure 1:
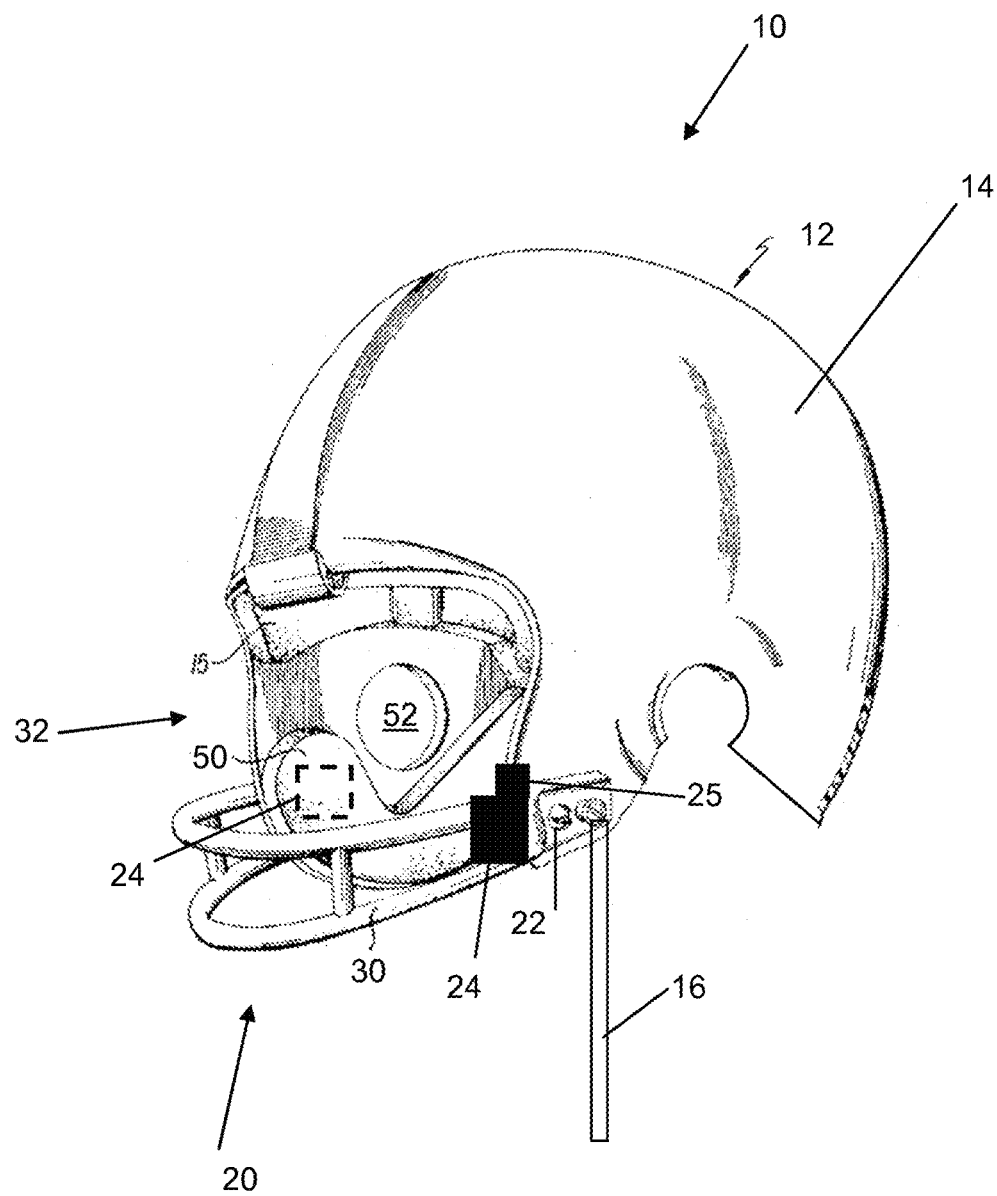
FIG. 1 is a perspective view of a protective headgear system.
Figure 10:
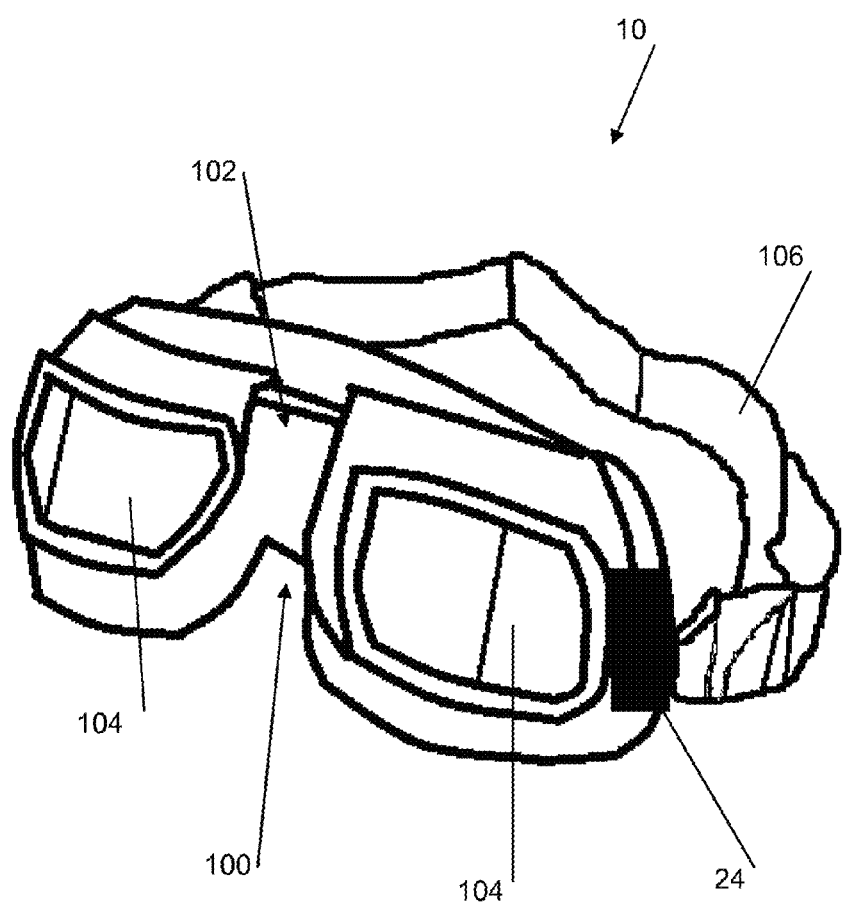
FIG. 10 is an embodiment of a protective eyewear accessory incorporating the impact detection device of FIG. 9.
Figure 11:
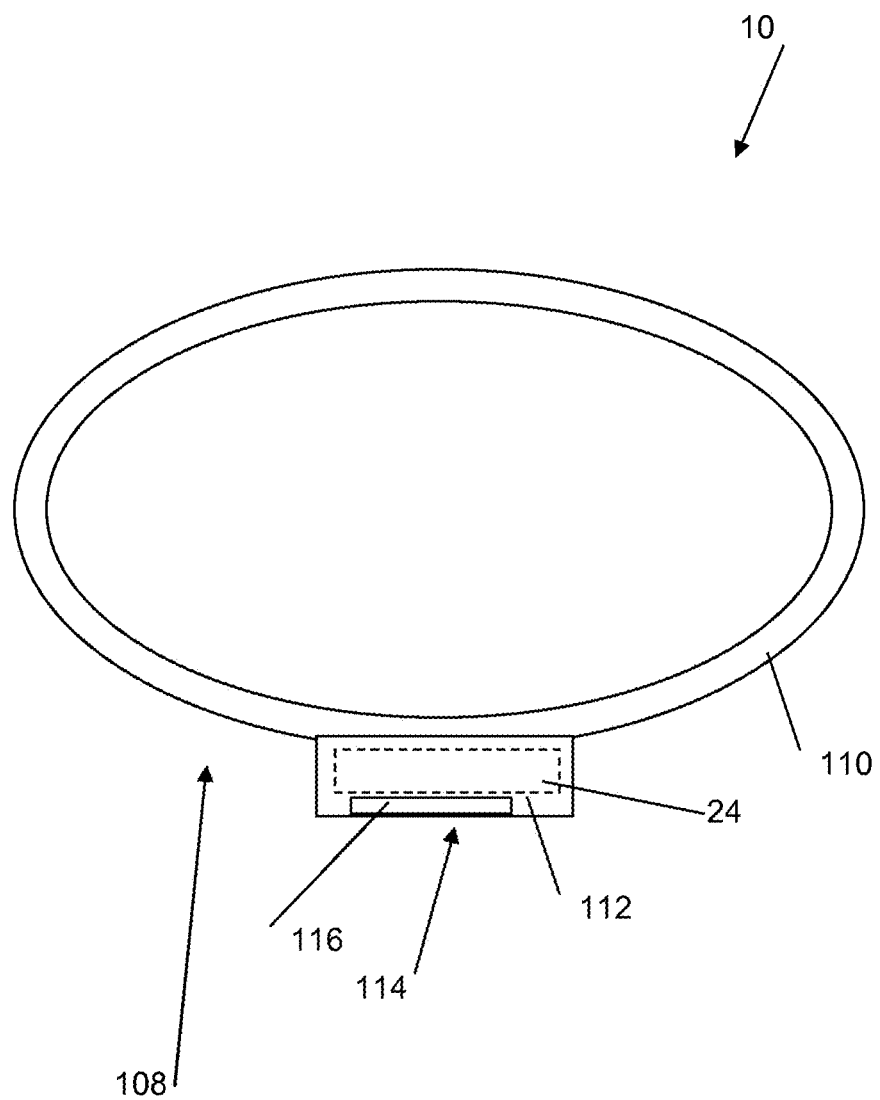
FIG. 11 is an embodiment of a protective headwear accessory incorporating the impact detection device of FIG. 9.

Referring to FIG. 1, shown is a protective headgear system 10 designed to help protect the wearer's skull from impacts with external objects by absorbing a portion of the mechanical energy of the impact and optionally protecting against penetration of the skull by the external object. The headgear system 10 can include a helmet 12 having an external shell 14 with interior padding 15 secured on the user's skull by a strap 16 (e.g. chin strap, back of head strap, etc.). The external shell 14 can be constructed as a rigid shell from plastics or other rigid composite materials (e.g. fiberglass reinforced with Kevlar or carbon fiber) and is used to protect the padding 15, typically comprising fabric and foam interiors for both comfort and protection (e.g. EPS "Expanded Polystyrene Foam"). The external shell 14 can be a continuous shell or can have holes or other cutouts (e.g. ear holes) that expose one or more portions of the wearer's skull for ventilation and/or weight reduction (of the helmet 12) purposes. It is also recognized that the external shell 14 can be comprised of non-rigid material such as exterior padding (e.g. such as those used in boxing and martial arts competitions). Referring to FIGS. 10 and 11, shown are alternative eyegear/headgear systems 10 for non-helmeted sports and activities that are also prone to concussive impact events, such that the alternative headgear systems 10 can include protective elements 20 such as goggles and headbands, as further described below.

Referring again to FIG. 1, the protective headgear system 10 can also have one or more protective elements 20 that can be releasably and rigidly secured to the helmet 12 via one or more fasteners 22, such that the one or more fasteners 22 are used to mechanically join or affix the protective elements) 20 and the helmet 12 together. Examples of the fasteners 22 can include mechanisms such as but not limited to: threaded fasteners (e.g. screws, bolts); one-time use adhesives; hook and loop fasteners; magnets; snaps; tab and slot (e.g. T-shaped or L-shaped cross-sectional male tab configured to releasably engage with a corresponding T-shaped or L-shaped cross-sectional female slot); buckles; belts; and other fasteners known in the art. Further, an impact detection device 24 is rigidly secured (e.g. via device fastener(s) 36—see FIG. 6) to the protective element 20 as an integrated assembly and thus to the protective headgear system 10, such that the impact detection device 24 is configured to measure and report force (e.g. G-force) caused by the impact, force direction caused by the impact, rotational acceleration caused by the impact, and/or duration of the impact. The impact detection device 24 can be configured as a g-force (for both translational and rotational forces/acceleration) monitoring system that provides for measurement and accumulation of impact data associated with a wearer of the protective element 20, via a unique identifier 25 of the impact detection device 24 associated with the wearer. As further described below, the impact detection device 24 can be programmable that detects and quantifies g force impacts in real-time and can include a Return to Play (RTP) interlock functionality, as further described below.

It is recognized that the protective element 20 and the impact detection device 24 are provided as the integrated assembly 35 (see FIG. 6), such that the device fasteners 36 of the impact detection device 24 are configured to connect with a compatible fastening element 37 of the protection element 20. The compatible fastening element 37 can be a hole to receive a threaded fastener of the device fastener 36. The compatible fastening element 37 can be a prepared surface to receive an adhesive fastener of the device fastener 36. The compatible fastening element 37 can be one half of a two part fastener of the device fastener 36. Examples of two part fasteners are fasteners such as but not limited to: hook and loop fasteners; magnets; snaps; tab and slot (e.g. T-shaped or L-shaped cross-sectional male tab configured to releasably engage with a corresponding T-shaped or L-shaped cross-sectional female slot); buckles; belts; and other known fasteners. It is recognized that the device fasteners 36 (and compatible fastening elements 37) can provide a releasably secure connection between the impact detection device 24 and the protective element 20, such that the impact detection device 24 can be detached from the protective element 20 subsequent to the initial attachment via the fasteners 36,36. It is also recognized that the device fasteners 36 (and compatible fastening elements 37) can provide a fixed and secure connection between the impact detection device 24 and the protective element 20, such that once secured only destruction of the integrity of the fasteners 36,37 can result in detachment of the impact detection device 24 from the protective element 20. As further described below, the impact detection device 24 is configured to determine the potential severity of the impact experienced by the protective headgear system 10 against one or more impact thresholds (e.g. indicative of potential concussion occurrence), and to make this determination available to people (e.g. coach, parent, trainer, employer, manager, etc.) associated with the wearer. In particular, the impact detection device 24 (see FIG. 6) has one or more lighting elements 62 (e.g. Light Emitting Diode—LED) that are positioned on an exterior housing 60 of the impact detection device 24, such that in detection of a possible concussion causing force impact to the player wearing the helmet 12 (see FIG. 1), the light element 62 becomes illuminated and visible to other people (e.g. coaching staff, spectators, other team players, fellow employers, etc.). It is recognized that the configuration of the protection element 20 and the impact detection device 24 is such that once the protection element 20 is installed on the helmet 12 via the fasteners 22 (see FIG. 1), the light element 62 is exposed and visible to the other people during activity of the wearer (e.g. player playing foot-ball). Alternatively or in addition to the light element 62, an audio element 64 (e.g. speaker) can be positioned on the exterior housing 60 of the impact detection device 24, such that in detection of a possible concussion causing force impact to the user wearing the helmet 12 (see FIG. 1), the audio element 64 activates and makes an audible alarm/sound that is audible to other people (e.g. coaching staff, spectators, other team players, etc.) near the wearer. It is recognized that the configuration of the protection element 20 and the impact detection device 24 is such that once the protection element 20 is installed on the helmet 12 via the fasteners 22 (see FIG. 1), the audio element 64 is exposed so as not to muffle exposure of the alarm/sound to the other people during activity of the wearer (e.g. player playing football).

Figure 6:
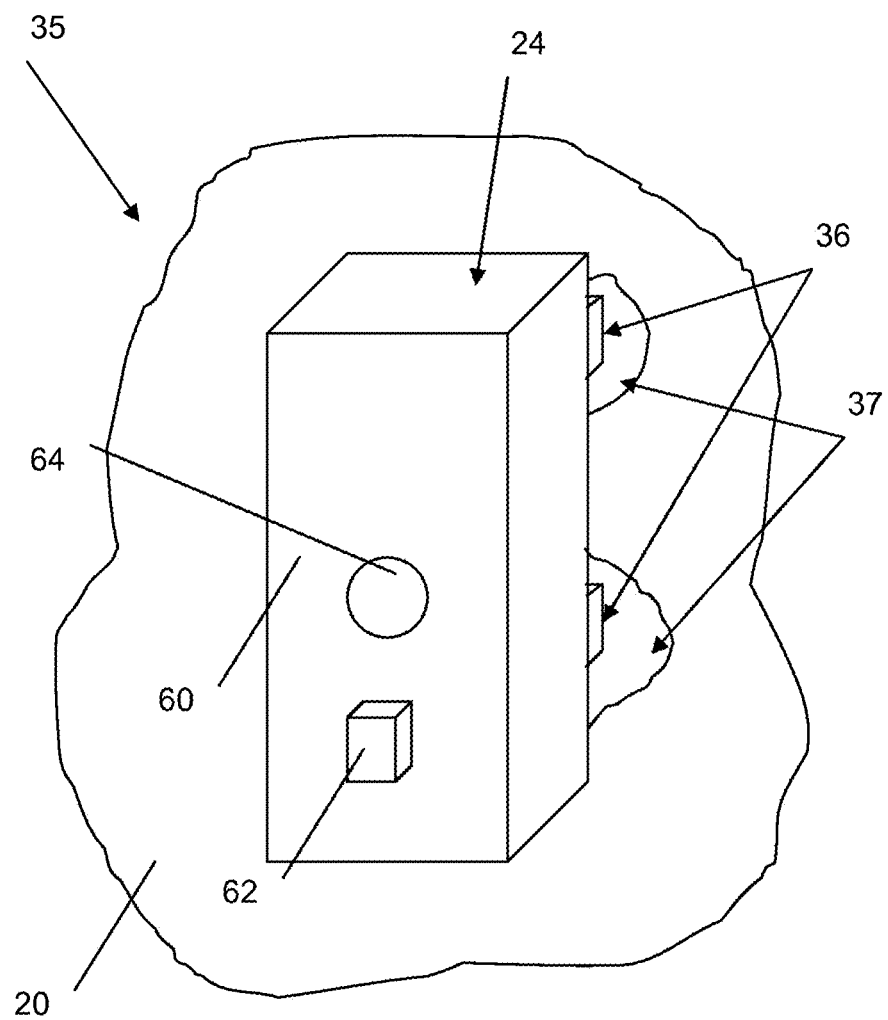
FIG. 6 is an example fastened combination of an impact detection device and the protection element of the system of FIG. 1.
Figure 7:
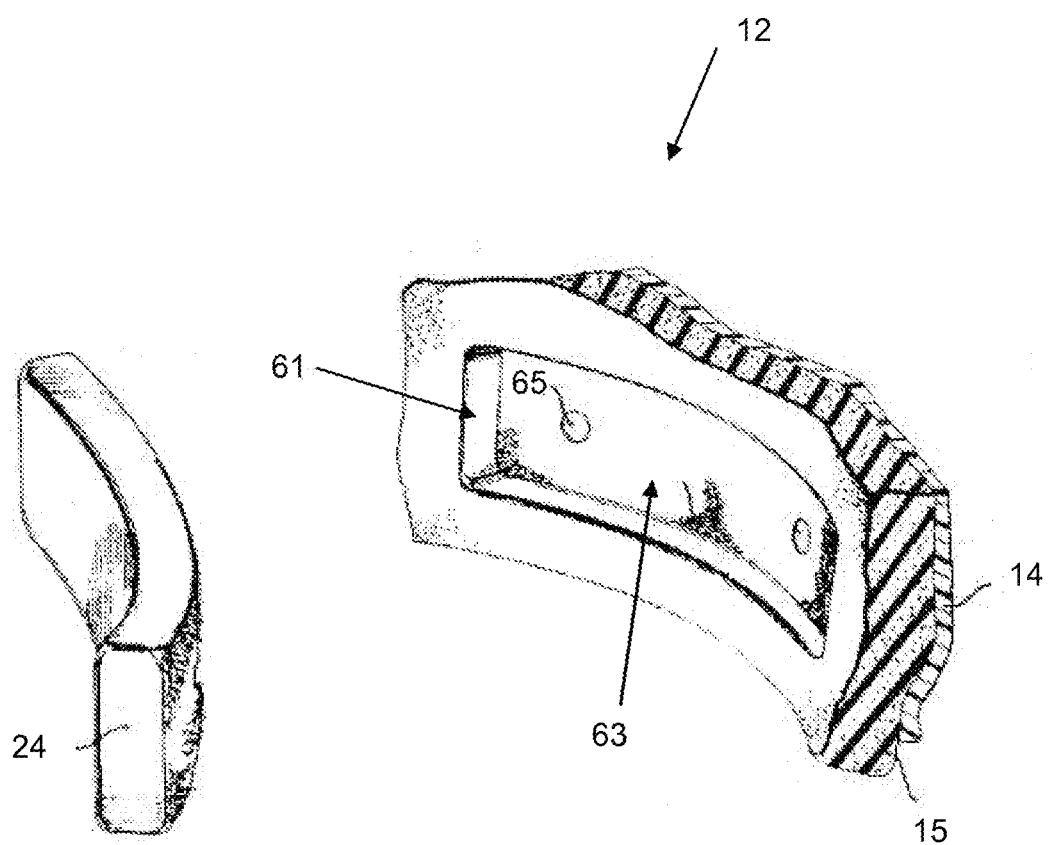
FIG. 7 is a further embodiment of a protection element of the system of FIG. 1.
Figure 8:
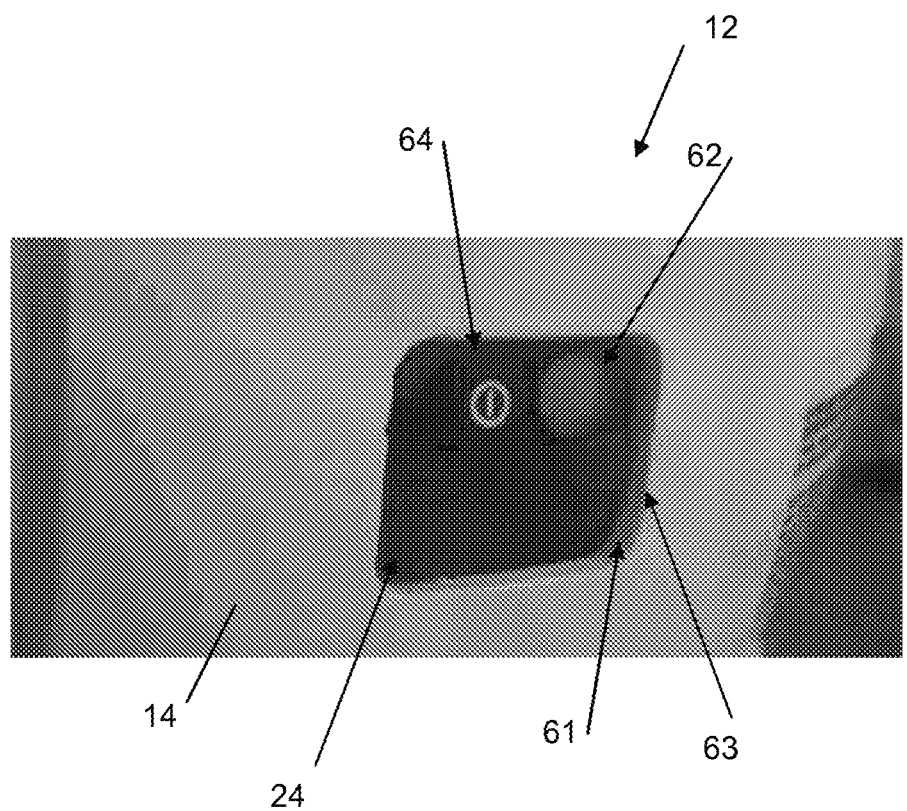
FIG. 8 is an alternative embodiment of the protection element of the system of FIG. 7.

As shown in FIG. 7, the impact detection device 24 can be embedded in a pocket 61 in the interior padding 15 anywhere in the helmet 12, such that the location of the impact detection device 24 is adjacent to a window 63 (e.g. transparent, translucent) that provides for transmission of illumination through the window 63 from the light element 62 (see FIG. 6). It is also recognized that the window 63 can have one or more apertures 65 that provide for transmission of audio through the window 63 from the audio element 64 (see FIG. 6). In this case, the protective element 20 is the structure of the pocket 61 with adjacent window 63 with apertures(s) 65, provided as an accessory of the helmet 12, such that the protective element 20 is fixedly attached to the helmet 12. As discussed above and not shown in FIG. 7 for illustrative convenience only, the impact detection device 24 is fastened to the protective element 20 via the device fasteners 36 (e.g. adhesive) and compatible fastening elements 37 (e.g. portion of window 63 compatible with providing a mounting surface for adhesive), see FIG. 6. FIG. 8 is an alternative embodiment of the protective element 20 provided as the pocket 61 with associated window 63.

One example application of the helmet 12 is a motorcycle helmet generally designed to distort in a crash (thus expending a portion of the energy otherwise destined for the wearer's skull). The density and the thickness of the padding 15 and/or the external shell 14 is designed to cushion or crush on impact to help prevent head injuries. However, once the helmet 12 experiences an impact, the helmet 12 may provide little subsequent protection at the impact location and therefore should be replaced, as the material(s) of the padding 15 and/or external shell 14 in the vicinity of the impact can be damaged beyond repair and thus would not be able to properly protect against a subsequent impact in the same location. Other examples of helmets 12 can include activities such as but not limited to: bicycle helmet; football helmet; boxing helmet; martial arts helmet; hockey helmet; lacrosse helmet; automobile or motorcycle racing helmet; water sports; winter sports; equestrian helmet; construction worker helmet; mining helmet; military helmet; etc. It can be an advantage of having the impact detection device 24 coupled (e.g. via device fasteners 36) to the protective element 20 as a combined assembly, rather than directly to the helmet 12 itself, so that the integrated assembly of protective element 20 and impact detection device 24 can be retained and re-used with a replacement helmet 12 in the event that component(s) (e.g. padding 15, external shell 14) of the helmet 12 has/have sustained damage due to impact. It is recognized that it is because of the releasably secure connection (when used) of the protective element 20 (via the fasteners 22) to the helmet 12, for example to the external shell 14, that the integrated assembly of protective element 20 and impact detection device 24 can be reused for other helmets.

Figure 2:
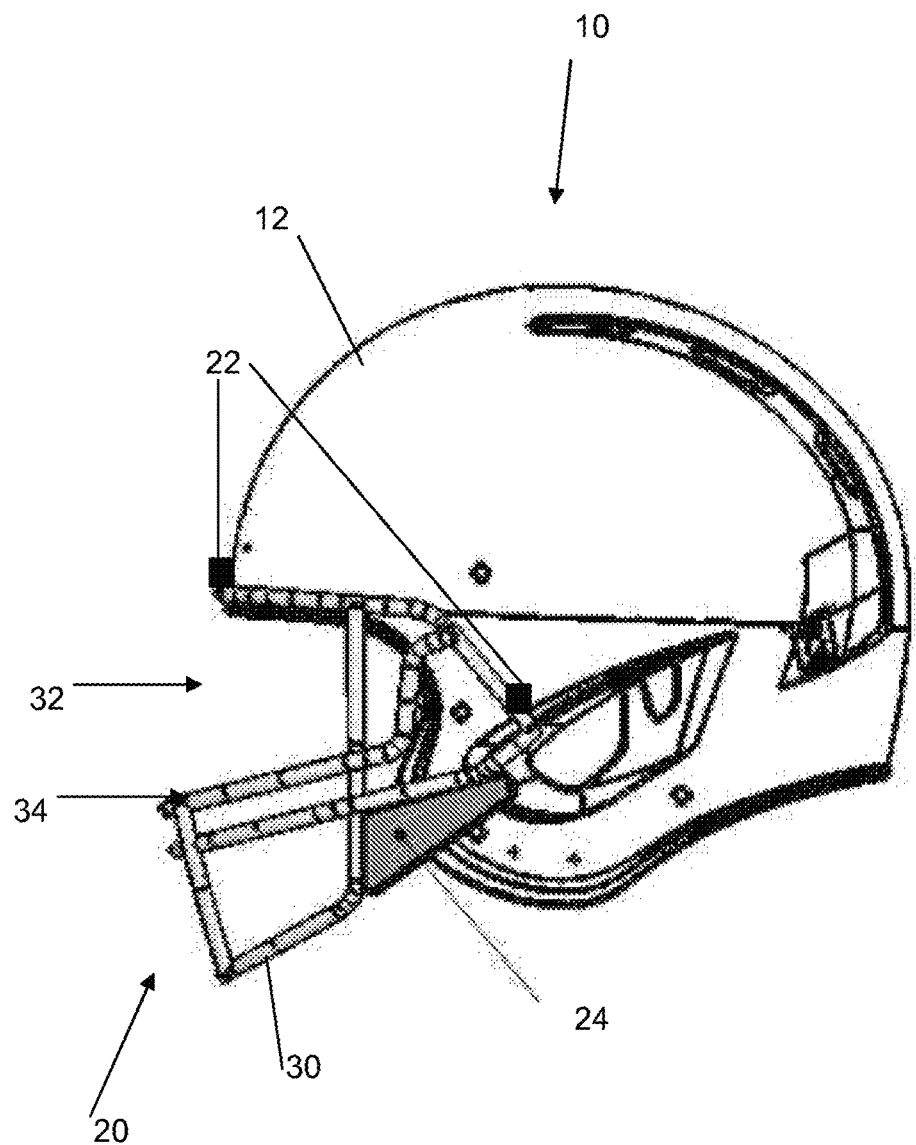
FIG. 2 is an embodiment of a protection element of the system of FIG. 1.

Referring to FIG. 2, the protective element 20 is rigidly connected (e.g. releasably secured) to the helmet 12 via the fasteners 22, such that mechanical energy of the impact exerted on the helmet 12 is transferred to the protective element(s) 20 via the fasteners 22. In this manner, mechanical energy of the impact is also experienced by the protective elements 20, and as such the impact(s) are detectable by the impact detection device 24. The acceleration characteristics, deceleration characteristics, or other impact characteristics of the impacts are measured by the impact detection device 24, such that these characteristics are determined as indicators of possible head trauma/concussion experienced by the wearer. It is recognized that characteristics of real-time impacts are detected and analyzed, as well as optionally cumulative impact history (i.e. aggregation of multiple impacts sustained over time). It is also recognized that the protective element 20 can be permanently affixed to the helmet 12 via appropriate fasteners 22 (e.g. rivets), however preferably the protective element 20 is releasably secured to the helmet 12 via appropriate fasteners 22.

Referring to FIGS. 1 and 2, the integrated protective element 20 with impact detection device 24 can be embodied as an accessory for the protective headgear system 10. One example of a protective element 20 is a face cage 30 having one or more fasteners 22 for releasable securing the face cage 30 to the helmet 12. The face cage 30 can be a type of protective visor including cage work 34 of thick wire or thin metal bars for positioning over at least a portion of a face opening 32 of the helmet 12. The face cage 30 is attached to the front of the helmet 12 via fasteners 22 to reduce potential of injury to the face of the wearer. The metal or composite mesh of the cage work 34 can covers the entire face of the wearer, although some portion (e.g. half) cages exist to help protect the eyes while allowing greater airflow. The bars of the cage work 34 are spaced far enough apart to provide for seeing through to action adjacent to the wearer but are close enough to stop objects (e.g. pucks and sticks in the case of hockey) from getting through to injure the face of the wearer. The impact detection device 24 is connected to the face cage 30 via a one or more device fasteners 36, see FIG. 6, such that the impact detection device 24 is rigidly coupled to the protective element 20 via the device fastener 36 so that mechanical energy of the impact experienced by the protective element 20 is also transferred and therefore detected by the impact detection device 24. Examples of the device fasteners 36 can include mechanisms such as but not limited to: threaded fasteners (e.g. screws, bolts); one-time use adhesives; hook and loop fasteners; magnets; tab and slot (e.g. T-shaped or L-shaped cross-sectional male tab configured to releasably engage with a corresponding T-shaped or L-shaped cross-sectional female slot); snaps; buckles; belts; and other fasteners as is known in the art. Positioning of the impact detection device 24 on the face cage 30 is preferably on a side of the face cage 30, so as not to obscure the wearer's field of vision.

Figure 3:
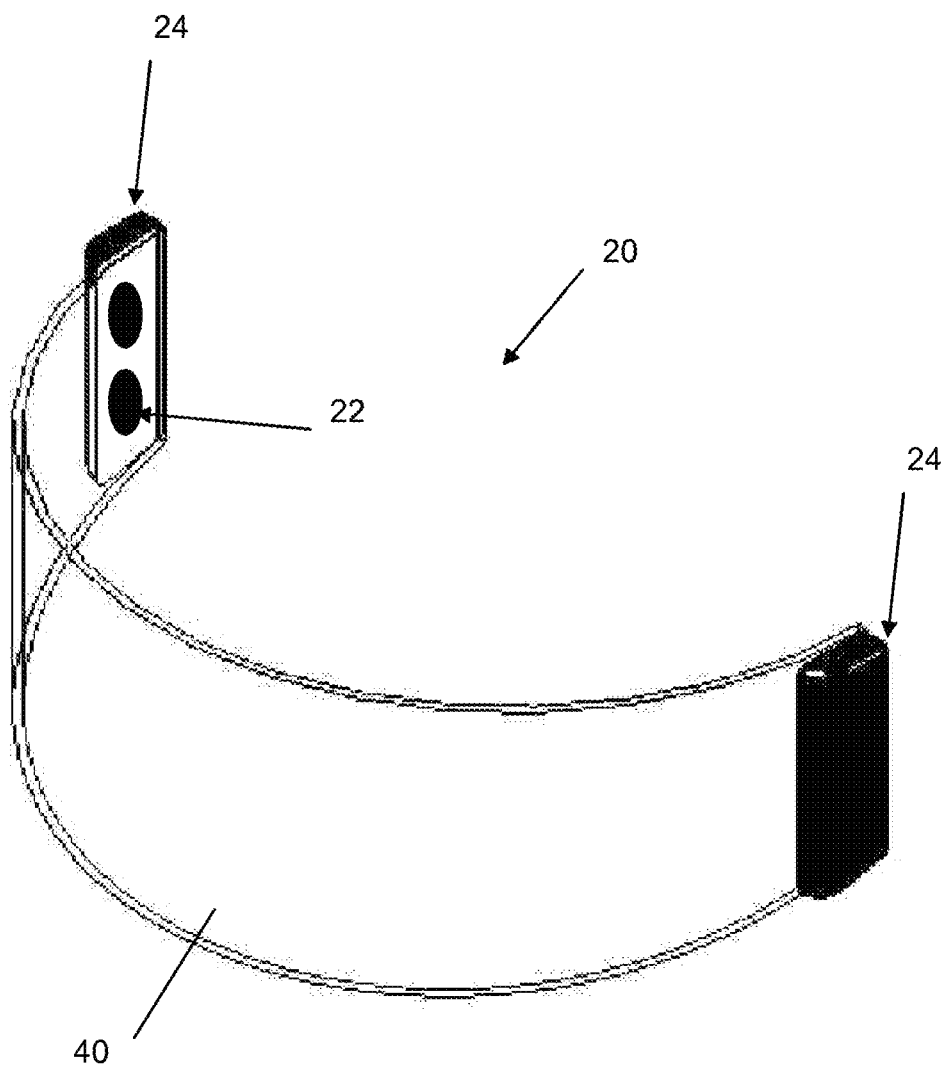
FIG. 3 is a further embodiment of a protection element of the system of FIG. 1.

Referring to FIGS. 1 and 3, shown is a further embodiment of the integrated protective element 20 with impact detection device 24 as a visor 40. The visor 40 has one or more fasteners 22 for releasable securing the visor 40 to the helmet 12. The visor 40 or shield is a protective device attached to the front of the helmet 12 to reduce potential of injury to the face of the wearer. Partial visors 40 can cover the upper half of the face, while full visors 40 (also known as face shields 40) cover the entire face of the wearer. The visors 40 can be made of a high impact-resistant plastic that is transparent, which can either be clear or shaded/tinted to help protect the eyes of the wearer from the sun or other bright lights. The impact detection device 24 is connected to the visor 40 via a one or more device fasteners 36, such that the impact detection device 24 is rigidly coupled to the protective element 20 via the device fastener 36 so that mechanical energy of the impact experienced by the protective element 20 is also transferred and therefore detected by the impact detection device 24. Examples of the device fasteners 36 can include mechanisms such as but not limited to: threaded fasteners (e.g. screws, bolts); one-time use adhesives; hook and loop fasteners; magnets; snaps; tab and slot (e.g. T-shaped or L-shaped cross-sectional male tab configured to releasably engage with a corresponding T-shaped or L-shaped cross-sectional female slot); buckles; belts; and other fasteners as is known in the art. Positioning of the impact detection device 24 on the visor 40 is preferably on a side of the visor 40, so as not to obscure the wearer's field of vision.

Figure 4:
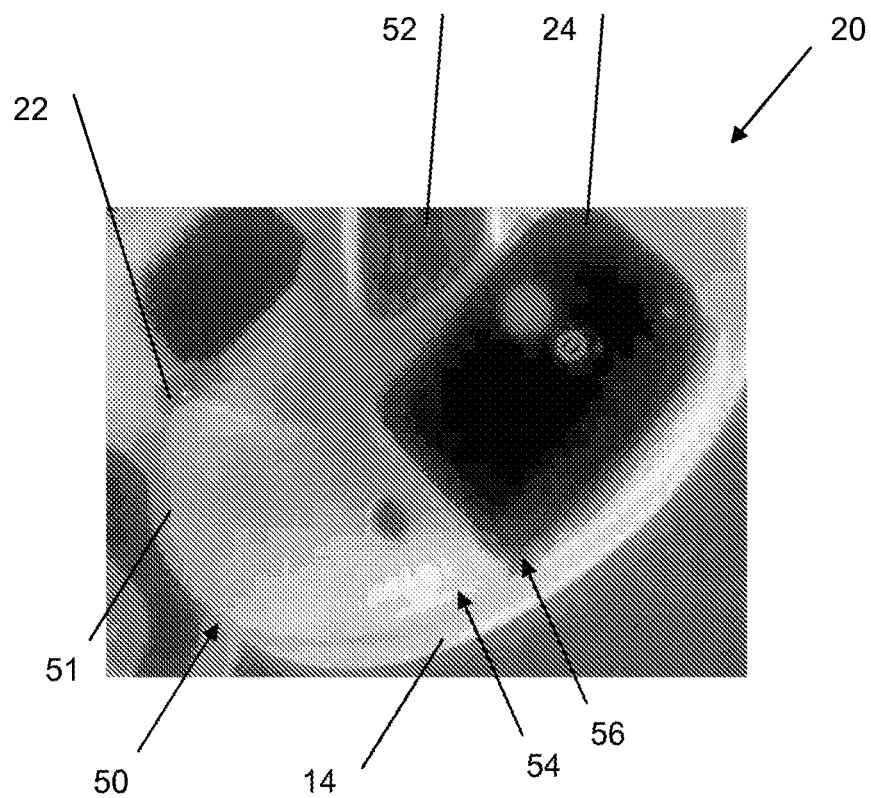
FIG. 4 is a further embodiment of a protection element of the system of FIG. 1.
Figure 5:
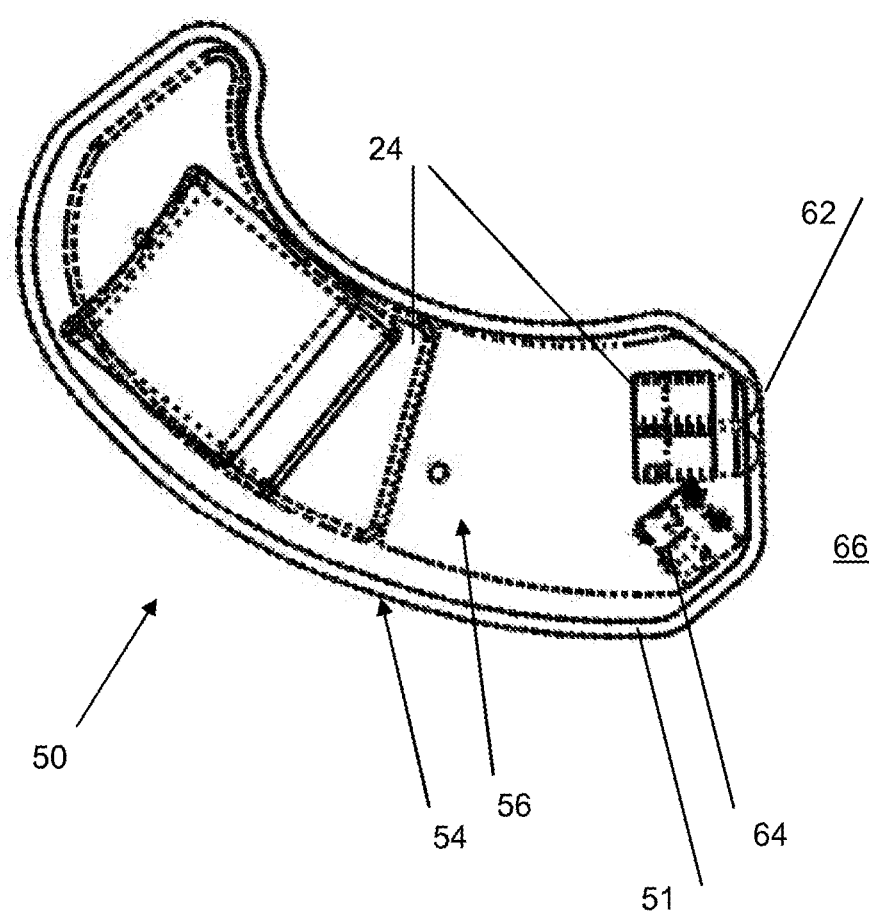
FIG. 5 is an alternative embodiment of the protection element of the system of FIG. 4.

Referring to FIGS. 1 and 4, shown is a further embodiment of the integrated protective element 20 with impact detection device 24 as a helmet pad 50, for example a cheek pad (also known as a jaw pad). These pads 50 provide for the helmet 12 to have a tight fit to the wearer's head. The cheek pads 50 are typically located just below the ear holes 52 in the helmet 12 and are usually fastened to the inside of the external shell 14 via fasteners 22 (e.g. hook and loop fasteners or snaps). These pads 50 are typically releasably secured to the helmet 12 via the fasteners 22 and are used to provide a customized or enhanced fit of the helmet 12 to the wearer's head. For example, these pads 50 can be installed on the helmet 12 after the wearer has positioned the helmet 12 on their head and these pads 50 can also be removed prior to removal of the helmet 12 from the wearer's head. These pads 50 can be made of resilient padding material 54 including EPS foam, air bladders, and/or gel inserts. The impact detection device 24 is positioned in an interior 56 (shown by example as a cutout in a covering 51 of FIG. 4) of the pads 50 and is fastened to the pads 50 interior 56 via a one or more device fasteners 36 (not shown), such that the impact detection device 24 is rigidly coupled to the protective element 20 via the device fastener 36 so that mechanical energy of the impact experienced by the protective element 20 is also transferred and therefore detected by the impact detection device 24. Examples of the device fasteners 36 can include mechanisms such as but not limited to: threaded fasteners (e.g. screws, bolts); one-time use adhesives; hook and loop fasteners; magnets; snaps; buckles; belts; and other fasteners as is known in the art. As shown in FIG. 5, the pad 50 has a complete padded cover 51 containing the impact protection device 24 (shown in dotted lines) in the interior 56. Also provided is an aperture 66 in the cover 51 so as to provide for exposure of the light element 62 (if present) to the helmet exterior 66. Also provided is an aperture 66 in the cover 51 so as to provide for exposure of the audio element 64 (if present) to the helmet exterior 66. Accordingly, the pad 50 can be positioned next to the skull and/or jaw/cheek of the helmet 12 wearer so that the padded cover 51 is in contact with the skin/hair of the helmet 12 wearer, for wearer comfort. Therefore the impact protection device 24 is contained within the interior 56 and thus not exposed to direct contact with the skin/hair of the helmet 12 wearer, while at the same time providing for exposure of the element 62,64 to the exterior 66 for observation (e.g. audibly, visibly) by the others in view/hearing of the player. It is also recognized that the cover 51 of the pad 50 may not completely encase the impact protection device 24 (i.e. have openings—not shown) in those areas that are configured as non-adjacent to the skin/hair of the helmet 12 wearer once the pad 50 is installed in the helmet 12 via the fasteners 22.

Figure 9:
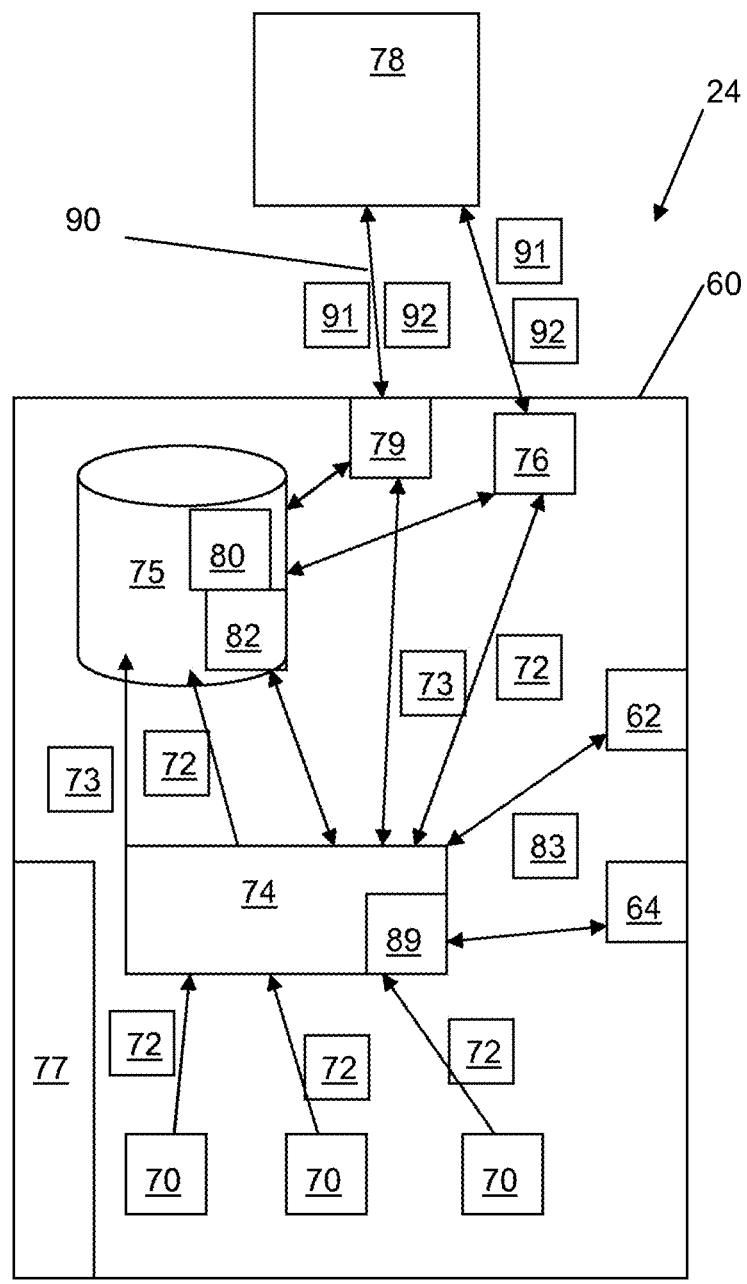
FIG. 9 is an example configuration of the impact detection device of FIG. 1.

Referring to FIG. 10, shown is an example of an integrated protective sports accessory 10 comprising a protective eyewear element 100 including a frame 102 having a pair of lenses 104 for protecting an area surrounding the eyes of the wearer and a strap 106 for affixing the protective eyewear element to the head of the wearer. The integrated protective sports accessory 10 also has the impact detection device 24 integrated with the protective eyewear element 100 via one or more device fasteners 36 (see FIG. 6) such that a portion of the protective eyewear element 100 has a compatible fastening element 37 to that of the one or more device fasteners 36 so that the impact detection device 24 is rigidly attached to the protective eyewear element 100 (e.g. to the frame 102). Referring to FIG. 9, the impact detection device 24 has: the housing 60, one or more sensors 70 within the housing 60 for sensing the impact event of the wearer when wearing the protective eyewear element 100 and for producing sensor data 72; the alarm element 62,64 coupled to the housing 60 such that the alarm condition produced by the alarm element 62,64 is detectable by one or more persons near the wearer; and the processor 74 within the housing 60 for processing the sensor data 72 against the impact threshold 82 and for producing the alarm condition signal for expression by the alarm element as the alarm condition. Positioning of the impact detection device 24 on the protective eyewear element 100 is preferably on a side of the protective eyewear element 100, so as not to obscure the wearer's field of vision. It is recognized that the protective eyewear element 100 is advantageous for those activities (e.g. sports) in which a helmet is not used.

Referring to FIG. 11, shown is a further embodiment of an integrated protective sports accessory 10 comprising: a protective headwear element 108 including a band 110 for affixing the protective headwear element 108 to the head of the wearer and a pocket 112 attached to the band 110, the pocket 112 configured for receiving therein the impact detection device 24 (shown in dotted lines) and having a window 114 positioned on the pocket 112 suitable for exposing (e.g. visually, audibly, etc.) the impact detection device 24 to an external environment of the protective headwear element 108. The impact detection device 24 is integrated with the protective headwear element 108 as positioned in the pocket 112 and retained therein via a pocket closure mechanism 116 such that the impact detection device 24 is rigidly coupled to the band 110. The pocket closure mechanism 116 can be configured as any number of mechanisms such as but not limited to: a fastened (e.g. hook and loop) fold covering an opening of the pocket 112, a slit in a sidewall of the pocket 112 of a dimension suitable to provide for insertion of the impact device 24 within the pocket 112 interior, etc. Referring to FIG. 9, the impact detection device 24 has: the housing 60; one or more sensors 70 within the housing for sensing an impact event of the wearer when wearing the protective headwear element 108 and for producing sensor data 72; the alarm element 62,64 coupled to the housing 60 such that the alarm condition produced by the alarm element 62,64 is detectable by one or more persons near the wearer through the window 114; and the processor 74 within the housing 60 for processing the sensor data 72 against the impact threshold 82 and for producing an alarm condition signal for expression by the alarm element 62,64 as the alarm condition.

In the pocket 112 attached to the band 110, the location of the impact detection device 24 is adjacent to the window 114 (e.g. transparent, translucent) that provides for transmission of illumination through the window 114 from the light element 62 (see FIG. 6). It is also recognized that the window 114 can have one or more apertures (not shown) that provide for transmission of audio through the window 114 from the audio element 64 (see FIG. 6). As discussed above and not shown in FIG. 7 for illustrative convenience only, the impact detection device 24 can be fastened to the protective headwear element 108 via the device fasteners 36

(e.g. adhesive) and compatible fastening elements 37 (e.g. portion of window 114 compatible with providing a mounting surface for adhesive), see FIG. 6.

Figure 12:
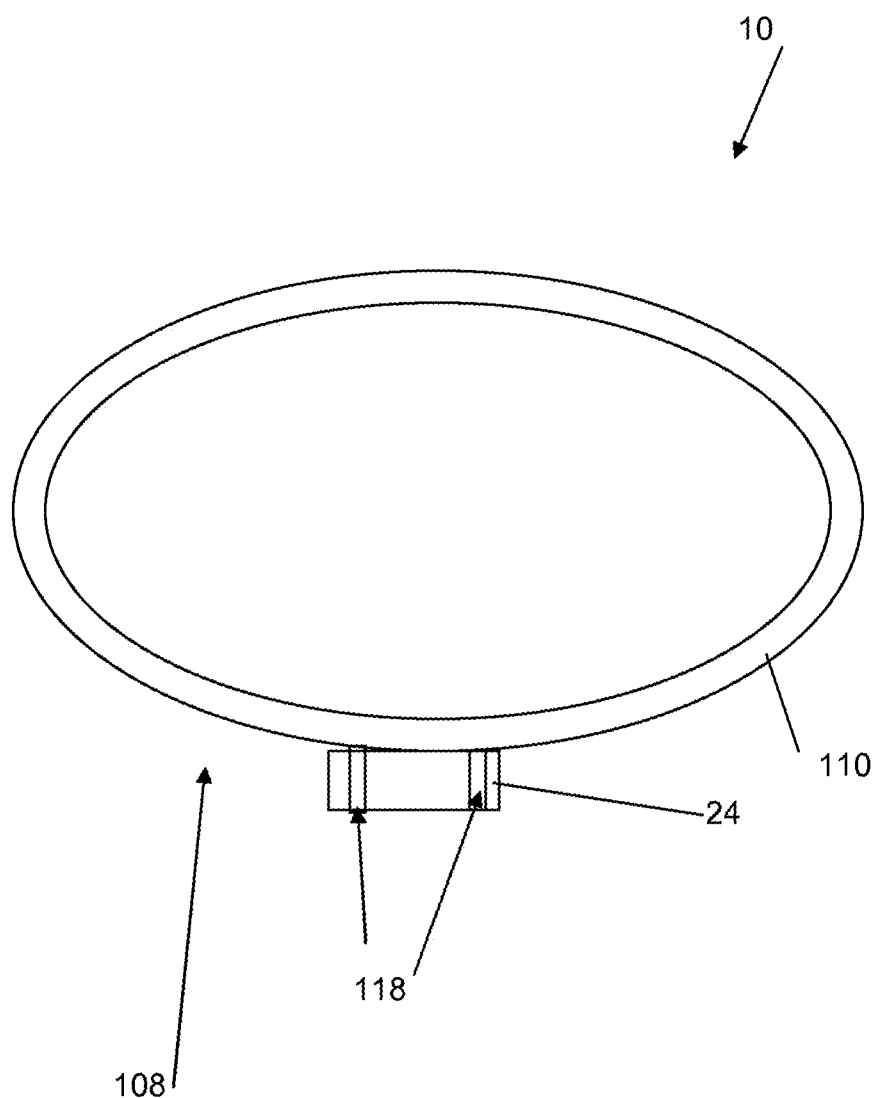
FIG. 12 is a further embodiment of the protective headwear accessory of FIG. 11.

An alternative embodiment shown in FIG. 12 is where one or more resilient (e.g. elastic) retaining bands 118 are positioned on the band 110 for retaining the impact detection device 24 to the band 110, once the impact detection device 24 is inserted into the retaining bands 118. It is recognized that the impact detection device 24 can be fastened to the retaining bands 118 and/or the ban 110 via the device fasteners 36 (e.g. hook and loop) and compatible fastening elements 37 (e.g. hook and loop), see FIG. 6.

Impact Device 24 Example Configuration

Referring to FIGS. 1 and 9, shown is an example configuration of the impact detection device 24 that is provided as part of an integrated protective accessory for the helmet 12, configured on a protective element 20 for rigidly attaching to the external shell 14 of the helmet 12 via one or more fasteners 22. The impact detection device 24 (as shown in FIG. 6) is integrated with the protective element 20 via one or more device fasteners 36 such that a portion of the protective element 20 has a compatible fastening element 37 to that of the one or more device fasteners 36 so that the impact detection device 24 is rigidly attached to the protective element 20.

The impact detection device 24 has the housing 60 (e.g. providing encapsulation for internal components to provide for shock and moisture resistance) for mounting therein (or thereon) one or more sensors 70 for sensing the impact event experienced by the player when wearing the helmet 12. The sensors 70 produce sensor data 72 that can be provided to a processor 74 for processing the sensor data 72 on-board the impact detection device 24, which is coupled to a storage device 75 configured for storing the sensor data 72, storing processing results 73 of the sensor data 72, and/or storing operating system instructions 80 for the processor 74 and other device hardware (e.g. alarm elements such as lighting element 62 and audio element 64). The alarm elements 62,64 are coupled to the housing such that the alarm condition produced by the alarm element 62,64 is detectable by one or more persons near the wearer. The impact detection device 24 can also have a wireless communication device 76 (e.g. 2.4 GHz ISM band) for transmitting the obtained sensor data 72 to a remote computer 78 within range of the wireless communication device 76. These transmissions can be in real-time for all detected impacts and/or only for transmission of those impacts that have exceeded one or more thresholds 82. The impact detection device 24 also has a battery 77 (e.g. rechargeable lithium ion) used to power various electrical components, such as the processor 74, the alarm elements 60,62, the storage device 75, and the wireless communication device 76.

The one or more thresholds 82 can be programmed as instructions 80 for use by the processor 74 to compare the sensor data 72 for each detected impact to: a Hit Injury Criteria (HIC) threshold 82; a GAAD Severity Impact (GSI) threshold 82; a linear force/acceleration magnitude threshold 82; a rotational force/acceleration magnitude threshold 82; a force/acceleration impact location and/or direction threshold 82 (e.g. specific impact locations and/or directions can warrant special attention—for example impacts causing compressive spine events, impacts laterally to the neck, etc.); and/or sensed temperatures past a predefined maximum temperature threshold 82. The processor 74 is mounted within the housing and is configured for processing (e.g. comparing) the sensor data 72 against an impact threshold 82 and for producing an alarm condition signal 83 for expression by the alarm element 62,64 as an alarm condition. When the processor 74 has determined that the sensor data 72 is indicative of an impact that has exceeded one or more thresholds 82, based on the force to threshold 82 comparison, the processor 74 is programmed to activate the alarm element(s) 62,64. The processing data 73 that is representative of the detected force to threshold 82 comparison can also be exported from the impact detection device 24 to the remote computer 78 using a wired connection (e.g. via a USB or other data transfer protocol) port 79. The processing data 73 that is representative of the detected force to threshold 82 comparison can also be exported from the impact detection device 24 to the remote computer 78 using the wireless communication device 76.

The sensors 70 (e.g. in conjunction with the processor 74) can be programmed to detect and record all detected impacts and/or to only record those detected impacts that exceed one or more of thresholds 82. As such, it is recognized that the quantitative value(s) of the threshold(s) can be selected or otherwise programmed via the processor 74, thus providing for user selectable threshold(s) 82. In terms of sensors 70, the sensors 70 can include a gyroscope (e.g. tri-axial) measuring rotational acceleration (e.g. of up to +/−2000 degrees per second at 750 Hz sample rate). The gyroscope 70 provides sensor data 72 indicative of force/acceleration representative of orientation and rotation, thus providing more robust sensor data 72 for increased recognition of movement within a 3D space of the wearer of the impact detection device 24. The gyroscope 70 is a device for measuring orientation and force/acceleration due to changes in rotational attitude of the impact detection device 24, based on the principles of angular momentum. Mechanically, the gyroscope 70 can be a spinning wheel or disk in which the axle is free to assume any orientation. Although this orientation does not remain fixed, it changes in response to an external torque much less and in a different direction than it would without the large angular momentum associated with the disk's high rate of spin and moment of inertia. Since external torque is minimized by mounting the device in gimbals, its orientation remains nearly fixed, regardless of any motion of the platform on which it is mounted. Gyroscopes 70 based on other operating principles also exist, such as the electronic microchip-packaged Micro Electro-Mechanical System (MEMS) gyroscope devices that use a vibrating element to produce the sensor data 72, a vibrating structure gyroscope (VSG) that uses a resonator made of different metallic alloys, solid-state ring lasers, and fiber optic gyroscopes (FOG) that use the interference of light to detect mechanical rotation in a coil of optical fiber. It is recognized that concussive effects of rotational acceleration can be greater that the concussive effects of linear acceleration.

Another sensor type 70 is one or more high G accelerometers measuring translation (e.g. single axis or tri-axis x-y-z) of g-force impacts for G forces up to 205 Gs (e.g. 50 to 200 G sensing) by transforming detected linear translation into a proportional voltage. The g scale of the high G accelerometers can be at least an order of magnitude greater than the low G sensors. The g scale of the high G accelerometers can be two orders of order of magnitude greater than the low G sensors. For example, the high G accelerometers can be for measuring 300+G force impacts and could be configured for measuring 400+ G force impacts. Accelerometers 70 are available to detect magnitude and direction of the proper acceleration (or g-force), as a vector quantity, using example mechanisms of piezoelectric, piezoresistive and/or capacitive components that convert the sensed mechanical motion into an electrical signal (e.g. voltage proportional to the amount of force sensed). Some accelerometers 70 can use the piezoelectric effect, as they can contain microscopic crystal structures that get stressed by accelerative forces, which causes a voltage to be generated. Another accelerometer 70 configuration is through sensing changes in capacitance, such that for two or more micro structures next to each other, they have a certain predefined capacitance between them. As an accelerative force moves one of the structures, then the capacitance will change and additional sensor circuitry can convert from capacitance to voltage that is representative of the capacitance change. Other alternative accelerometer 70 configurations can include piezoresistive effect, hot air bubbles, and light. Other accelerometers can include separate lower G sensors (e.g. +/−2,4,8, 16 G) accelerometers 70 used to measure accelerometer translation of x-y-z calculations for bio-metric data collection (e.g. 48 Hz sampling rate). Another sensor 70 type is a temperature sensor used to provide temperature sensor data 72 to the processor 74 that could be indicative of potential heatstroke of the wearer when doing activity in higher temperature settings, such that the predefined threshold 82 would be a maximum temperature and/or maximum rate of temperature rise.

It is recognized that the processing results 73 can include data such as but not limited to: number of sensed impacts (e.g. number of impacts per session identified), date and time stamping of detected impacts, for example for both alarm condition impacts and non-alarm condition impacts; from record value to alarm points; severity of detected impact based on determined alarm condition by checking to see if the sensor data 72 exceeds a user selectable threshold 82 (e.g. calculation and identification of impacts within the alarm threshold (WTH)−WTH=10% of threshold); historical accumulation of a plurality of detected impacts for a session time period (e.g. a game, a race, a work shift, a defined portion of a day or days, etc.); calculation of duration of detected impact (e.g. force vs. time curve/data); representation of linear acceleration for the detected impact in one or more spatial dimensions (e.g. 3); location of the detected impact on the wearer's body, the helmet 12 and/or protective element 20; degree of severity indication for the detected impact (e.g. color or number coded impact—green, yellow, red based on severity of impact trough comparison to threshold 82); Hit Injury Criteria (HIC) calculation with each impact; GAAD Severity impact (GSI) Calculation with each impact; linear and/or rotational spatial dimension calculations for the detected impact.

Alternatively, in the event where processing on-board is not desired, the sensor data 72 can be supplied to the wireless communication device 76 for transmitting the obtained sensor data 72 to the remote computer 78 within range of the wireless communication device 76. In further alternative, in the event where processing on-board is not desired, the sensor data 72 can be supplied to the storage device 75 for later retrieval (e.g. downloaded) via a data access port 79 (e.g. USB port).

The processor 74 of the impact detection device 24 can also be programmed to have a Return to Play (RTP) interlock feature 89, whereby once the alarm signal (or condition) has been activated (e.g. illumination by the light element 62 and/or audio by the audio element 64), the alarm condition cannot be turned off until certain data events have occurred. One example of the data event is where the sensor data 72 has been exported from the impact detection device 24 via a wired connection 90 between the data port 79 and the remote computer 78. The processor 74 receives an export command 91 (or acknowledgement of receipt of exported data) from the remote computer 78 and in response can turn off or otherwise deactivate the alarm element(s) 62,64, as a result of receiving and exporting the sensor data 72. Alternatively, the processor 74 (after exporting the sensor data 72 to the remote computer 78) can receive an alarm cancellation signal 92 from the remote computer 78 over the wired connection 90 and in response can deactivate the alarm element (s) 62,64. A further alternative embodiment of the data event is where the sensor data 72 has been exported from the impact detection device 24 via a wireless connection 94 between the wireless communication device 76 and the remote computer 78. This export of the sensor data 72 can be configured as either a data push or a data pull operation 91 between the impact detection device 24 and the remote computer 78. Upon export of the sensor data 72 via the wireless connection 94, the processor 74 can deactivate the alarm element(s) 62,64. Alternatively, upon export of the sensor data 72 via the wireless connection 94 and receipt of a deactivate signal from the remote computer 78, the processor 74 can deactivate the alarm element(s) 62,64. It is recognized that the export of the sensor data 72 to the remote computer 78 can provide for assessment and review of the sensor data 72 by a qualified professional (e.g. coach, trainer, or other medically trained professional) prior to allowing the wear to return to their activity (e.g. game).

Figure 13:
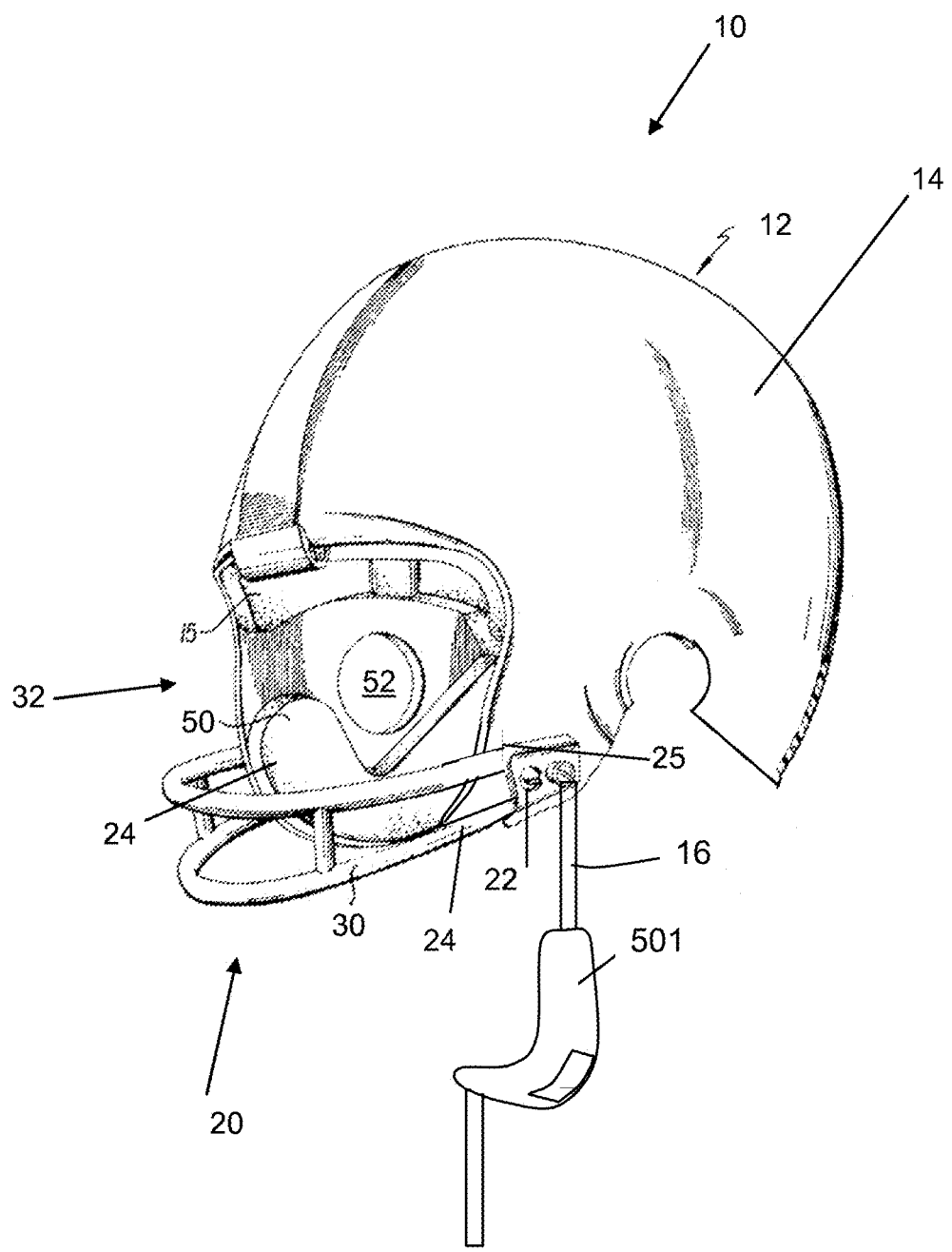
FIG. 13 is a perspective view of another embodiment of a headgear system.
Figure 14:
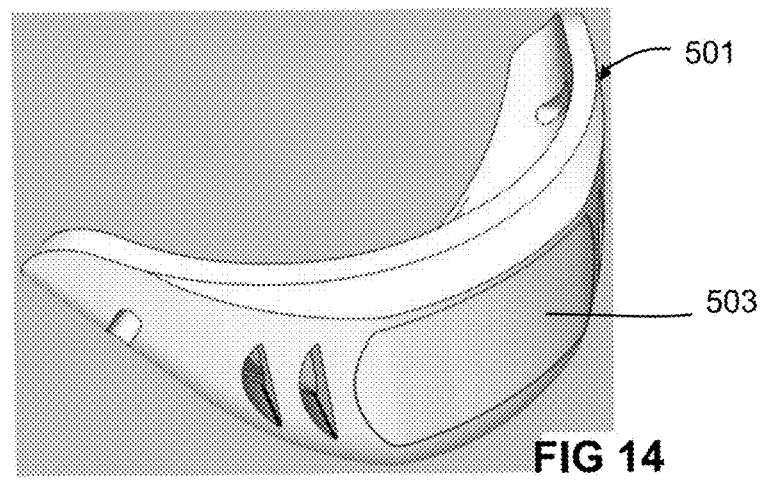
FIG. 14 is a perspective view of a chin guard from the headgear system shown in FIG. 13.
Figure 15:
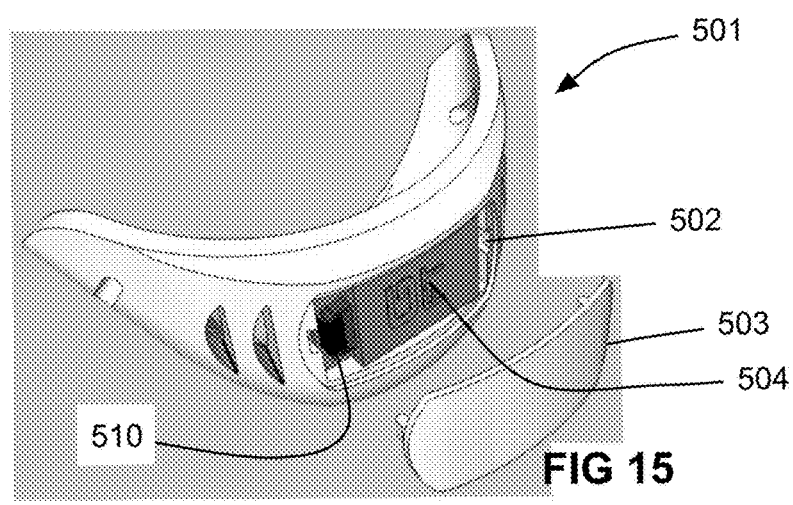
FIG. 15 is a perspective view of the chin guard shown in FIG. 14 with a cover removed.
Figure 16:
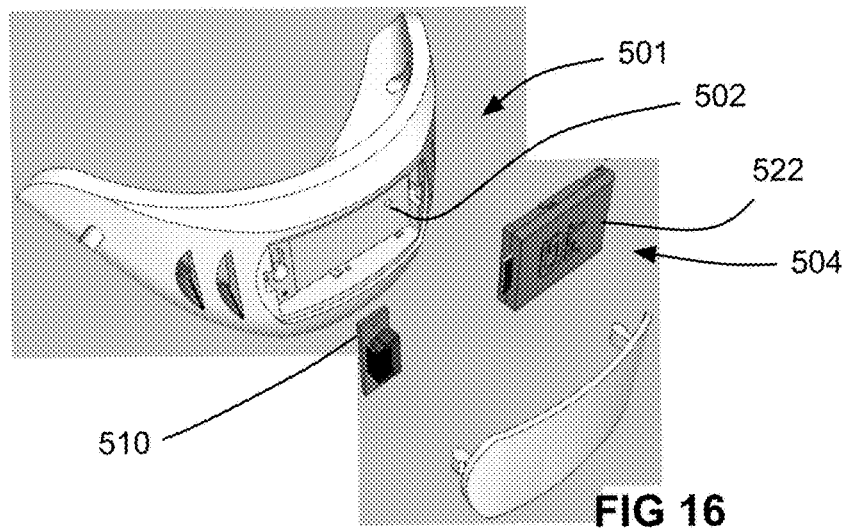
FIG. 16 is a perspective view of the chin guard shown in FIG. 14 with the cover and an impact detection device removed.

Referring to FIG. 13, shown is the protective headgear system 10 wherein the chin strap 16 has a chin guard 501 which is shown in more detail in FIG. 14. The chin guard 501 has a compartment 502 (FIG. 3) with a removable cover 503 for releasably holding an impact detection device 504 (FIGS. 15 and 16).

Figure 17:
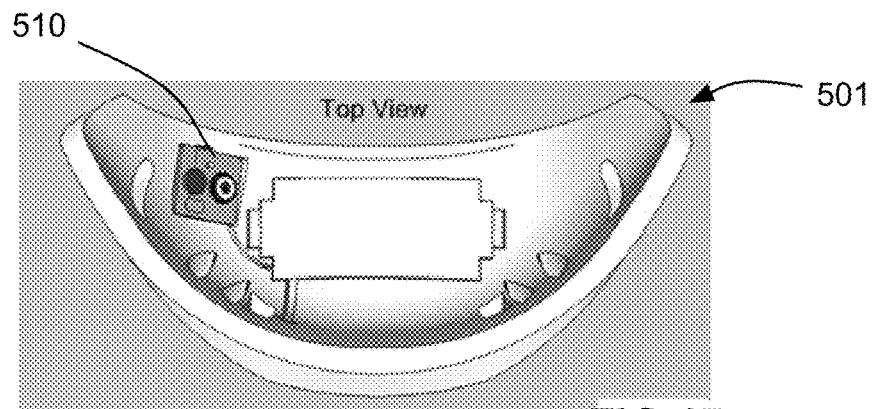
FIG. 17 is a top plan view of the chin guard shown in FIG. 14 showing a secondary module that cooperates with the impact detection device.
Figure 18:
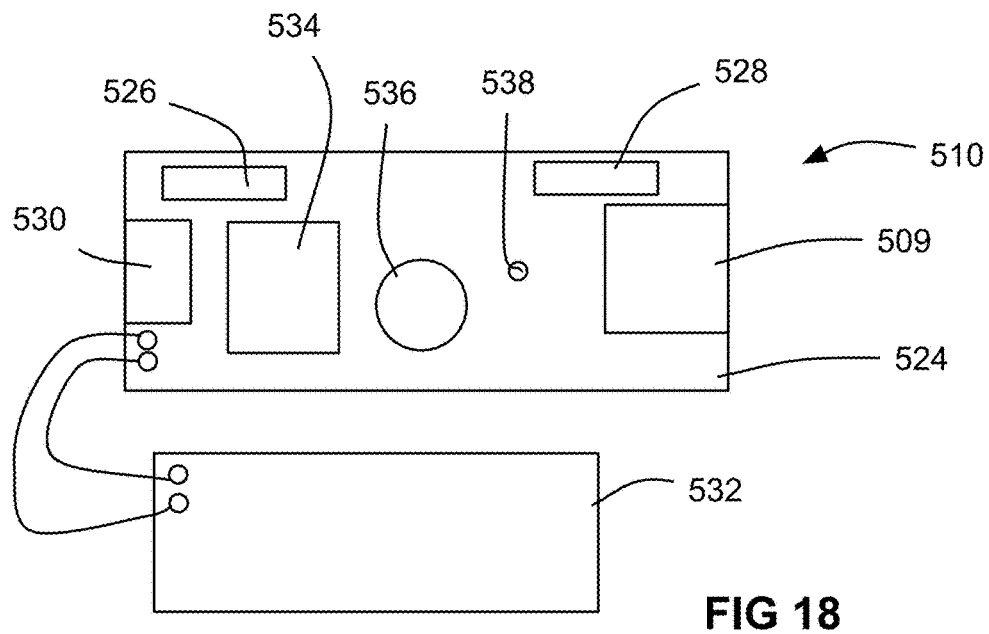
FIG. 18 is a schematic illustration of the secondary module.

A block diagram of the impact detection device 504 is shown in FIG. 18. The impact detection device 504 may include a first printed circuit board (PCB) 506, a main module connector 508 for connecting to a secondary module connector 509 (FIG. 19) on a secondary module 510 in the chin guard 502 (FIG. 17), a 3-axis accelerometer 512, which may be as described above in relation to the embodiment shown in FIGS. 1-12, the 3-axis gyroscope 514 which may be as described above in relation to the embodiment shown in FIGS. 1-12, a microcontroller 516 similar to that described above, a memory module 518 and a wireless communications transceiver 520, all of which are mounted to the PCB 506. A housing 522 (FIG. 16) is provided for shock and moisture protection of the aforementioned components.

Figure 19:
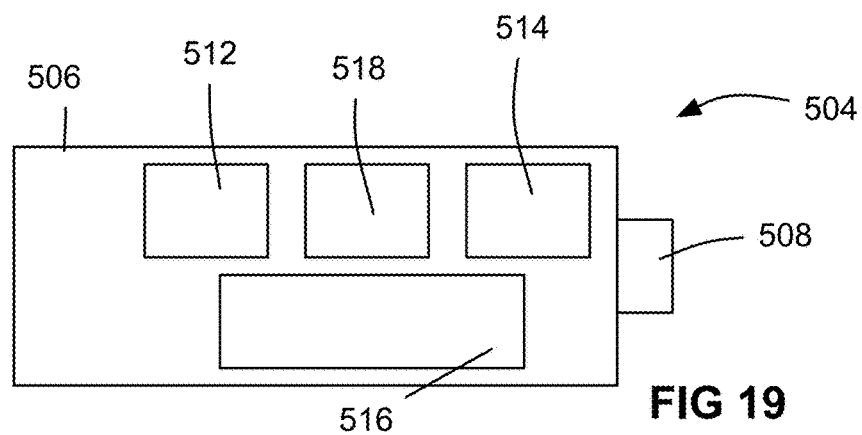
FIG. 19 is a schematic illustration of the impact detection device.

The secondary module 510 is shown in FIG. 19. The secondary module 510 includes a plurality of components including a second PCB 524, a temperature sensor 526, a proximity sensor 528, the secondary module connector 509, a micro-USB port 530, a battery 532, a power supply 534, a power switch 536, and an output device such as an LED 538, which are all mounted to the PCB 524.

Figure 20:
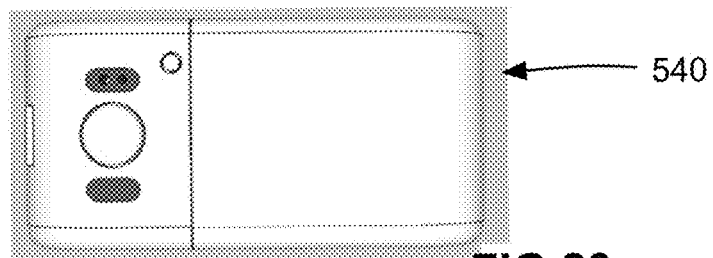
FIG. 20 is a top plan view of a module assembly housing that holds the secondary module and the impact detection device.
Figure 21:
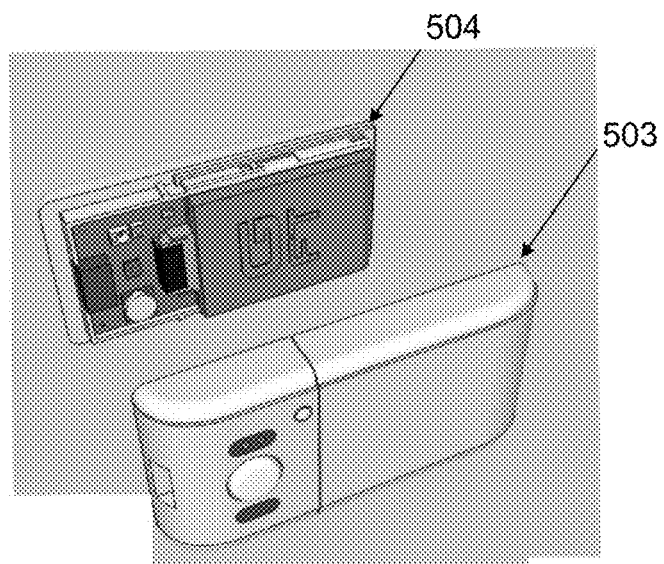
FIG. 21 is a perspective view of the module assembly housing shown in FIG. 20 with a cover of the housing removed.
Figure 22:
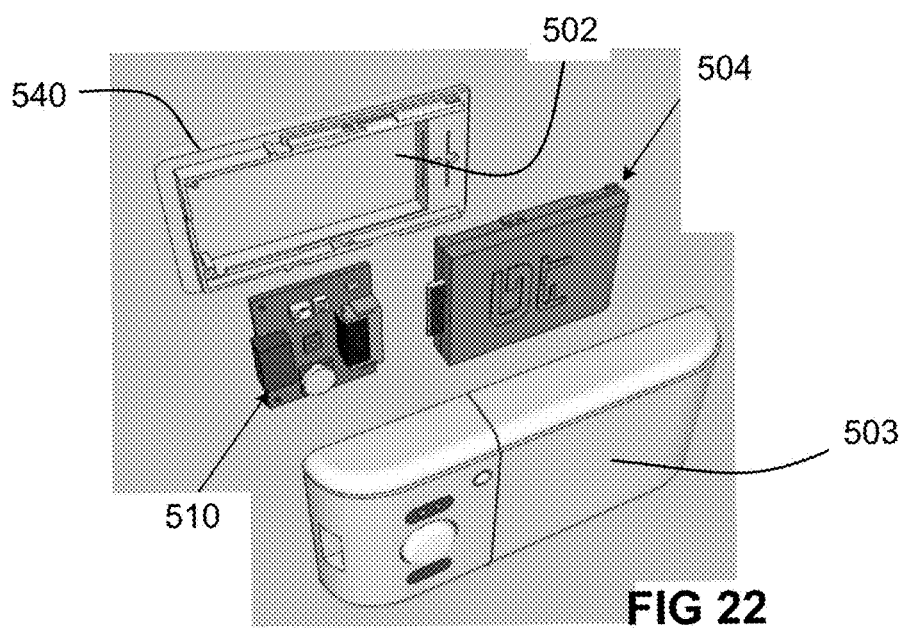
FIG. 22 is a perspective view of the module assembly housing shown in FIG. 20 with the cover, the secondary module and the impact detection device removed.

Several different components that are worn by the user during different activities may each contain a version of the secondary module 510 and may include a compartment 502 for receiving the impact detection device 504. For example, as shown in FIGS. 20-22, a module assembly housing 540 may be provided that is portable and may be adhered, inserted, connected or otherwise used wherever appropriate. The module assembly housing 540 includes the aforementioned compartment 502, the openable cover 503, and the secondary module 510 for receiving the impact detection device 504.

In the embodiment shown in FIG. 23, a headband 550 is shown with a headband strap 551 and a headband module housing 552. The housing 552, which is shown in FIGS. 24-26 includes a compartment 502 for holding the impact detection device 504 in releasable connection with the secondary module 510.

The battery 532 may be rechargeable (e.g. via the USB connector 530) and is connected to the PCB 524 to power both the secondary module 510 and the impact detection device 504. By keeping the battery 532 with the secondary module 510, the impact detection device 504 can remain small and the battery 532 can be shaped as needed to best fit within the shape of the accessory in which the secondary module 510 is installed in.

The temperature sensor 526 may be similar to the temperature sensor described above in relation to the embodiment shown in FIGS. 1-12. It is advantageous for the temperature sensor 526 to be in the secondary module 510 so that it can be individually calibrated as necessary to provide accurate temperature readings based on its position with its associated accessory. Because the impact detection device 504 is positioned in a different position relative to the wearer and because each housing has different thermal properties, a temperature sensor mounted to the impact detection device 504 might require calibration for each different accessory. By keeping the temperature sensor 532 in the secondary module 510 calibration is not required each time the impact detection device 504 is moved to a new accessory.

The proximity sensor 528 is positioned to detect the head of the wearer (or whatever body part of the wearer that the sensor 528 is positioned to be proximate to). By detecting the head of the wearer the proximity sensor can indicate to the impact detection device 504 that it is okay to read signals from the impact sensors (the accelerometer 512 and gyroscoper 514). By contrast, if the wearer is simply holding his helmet by the chin strap 16 and swinging it around or throwing it against something, the proximity sensor 528 would not sense the head of the wearer and would prevent the impact detection device 504 from recording this data, thereby preventing certain false positive readings for impacts that could otherwise occur. Like the temperature sensor, the proximity sensor 528 may be provided as part of the secondary module 510 so as to remain in a constant position in the accessory and so as to not require repeated recalibration when the impact detection device 504 is transferred from one accessory to another. The proximity sensor 528 need not be used only in an embodiment in which there is an impact detection device that is separate from a secondary module 510. It can be used in any suitable assembly that includes one or more of the impact sensors, the microcontroller and whatever other components are necessary.

In each case, the accessory (i.e. the chin guard 501, the module housing 540 and the headband module housing 552) includes an accessory housing, the impact detection device 504 and the secondary module 510. The impact detection device 504 includes at least one impact sensor selected from the group of sensors comprising the accelerometer 512 and a gyroscope 514, and the secondary module 510 includes at least the battery 532. The impact detection device 504 and the secondary module 510 together further include a microcontroller 516 and the memory 518. The impact detection device 504 is removably connectable to the secondary module 510 and is connectable to another secondary module 510 in another accessory.

Those skilled in the art will understand that a variety of modifications may be effected to the embodiments described herein without departing from the scope of the appended claims.

The invention claimed is:

1. An accessory for an activity, comprising:
an accessory housing; and
an impact detection device and a secondary module, wherein the impact detection device includes at least one impact sensor selected from the group of sensors comprising an accelerometer and a gyroscope, and wherein the secondary module includes a battery configured for powering both the impact detection device and the secondary module, and wherein the impact detection device and secondary module together further include a microcontroller, and a memory,
wherein the impact detection device is releasably connectable to the secondary module while the secondary module remains in the accessory housing and is connectable to another secondary module in another protective accessory.

2. An accessory for an activity as claimed in claim 1, wherein the protective member is a chin guard.

3. An accessory for an activity as claimed in claim 1, wherein the impact detection device includes both an accelerometer and a gyroscope.

4. An accessory for an activity as claimed in claim 1, wherein the secondary module includes the battery, and a power supply, a power switch for controlling power from the battery.

5. An accessory for an activity as claimed in claim 1, wherein the secondary module includes a temperature sensor configured for measuring a temperature of a wearer of the accessory.

6. An accessory for an activity as claimed in claim 1, wherein the secondary module an output device configured for indicating an alarm condition for the at least one impact sensor.

* * * * *